United States Patent
Kim et al.

(10) Patent No.: US 9,101,055 B2
(45) Date of Patent: Aug. 4, 2015

(54) METHOD OF MEASURING A THREE-DIMENSIONAL SHAPE

(71) Applicant: KOH YOUNG TECHNOLOGY INC., Seoul (KR)

(72) Inventors: Min-Young Kim, Seoul (KR); Bong-Ha Hwang, Incheon (KR)

(73) Assignee: KOH YOUNG TECHNOLOGY INC., Seoul (JP)

( * ) Notice: Subject to any disclaimer, the term of this patent is extended or adjusted under 35 U.S.C. 154(b) by 314 days.

(21) Appl. No.: 13/860,298

(22) Filed: Apr. 10, 2013

(65) Prior Publication Data

US 2013/0229509 A1    Sep. 5, 2013

Related U.S. Application Data

(62) Division of application No. 12/575,768, filed on Oct. 8, 2009, now Pat. No. 8,437,533.

(30) Foreign Application Priority Data

Oct. 13, 2008    (KR) .................. 10-2008-0100003

(51) Int. Cl.
*H05K 1/02*    (2006.01)
*G01B 11/25*    (2006.01)
(Continued)

(52) U.S. Cl.
CPC ............ *H05K 1/0269* (2013.01); *G01B 11/254* (2013.01); *G01B 11/2513* (2013.01); *G01B 11/28* (2013.01); *G01N 21/95607* (2013.01); *G06T 7/001* (2013.01); *G06T 7/0028* (2013.01); *G06T 7/0073* (2013.01); *G06T 7/60* (2013.01);
(Continued)

(58) Field of Classification Search
CPC .. G01B 11/2513; G01B 11/254; G01B 11/28; G01B 11/167; G01B 11/0633; G06T 3/0068; G06T 7/0004; G06T 7/0016; G06T 7/0024; G06T 7/0028; G06T 7/0073; G06T 7/60; G06T 2207/30141; H05K 1/0266; H05K 1/0269; H05K 1/0274; H05K 3/0008; H05K 2201/09918
See application file for complete search history.

(56) References Cited

U.S. PATENT DOCUMENTS 4,185,298 A * 1/1980 Billet et al. .................. 348/129
4,648,053 A * 3/1987 Fridge .......................... 382/147
(Continued)

FOREIGN PATENT DOCUMENTS

JP    58-021107    2/1983
JP    03-009249    1/1991
(Continued)

*Primary Examiner* — Manav Seth
(74) *Attorney, Agent, or Firm* — Kile Park Reed & Houtteman PLLC

(57) ABSTRACT

In order to measure a three-dimensional shape, feature information is read from a database. A board is transferred to a measurement position. A measurement head is transferred to an inspection area of the board. Light of a first lighting device for three-dimensional measurement and light of a second lighting device for two-dimensional measurement is illuminated onto the inspection area to photograph a first reflection image and a second reflection image that are reflected from the inspection area. The inspection area is realigned by comparing the feature information with at least one of the photographed first and second reflection images to inspect distortion of the inspection area. The realigned inspection area is inspected. Thus, the three-dimensional shape may be precisely measured.

7 Claims, 9 Drawing Sheets

(51) Int. Cl.
  *G01B 11/28* (2006.01)
  *G06T 7/00* (2006.01)
  *G01N 21/956* (2006.01)
  *G06T 7/60* (2006.01)

(52) U.S. Cl.
  CPC ............... *G06T 2207/10028* (2013.01); *G06T 2207/30141* (2013.01)

(56) References Cited

U.S. PATENT DOCUMENTS

| | | | | |
|---|---|---|---|---|
| 4,654,583 | A | * | 3/1987 | Ninomiya et al. ............ 382/147 |
| 5,161,202 | A | * | 11/1992 | Kitakado et al. ............. 382/147 |
| 5,166,985 | A | * | 11/1992 | Takagi et al. ................ 382/150 |
| 5,459,794 | A | * | 10/1995 | Ninomiya et al. ............ 382/145 |
| 5,680,207 | A | * | 10/1997 | Hagiwara .................. 356/237.3 |
| 6,072,899 | A | * | 6/2000 | Irie et al. ...................... 382/149 |
| 6,777,677 | B2 | * | 8/2004 | Nozoe et al. ...................... 850/9 |
| 7,034,298 | B2 | * | 4/2006 | Miyai et al. .................... 250/310 |
| 7,042,172 | B2 | * | 5/2006 | Dowling et al. ............... 315/294 |
| 7,315,361 | B2 | * | 1/2008 | Schramm et al. ........... 356/237.1 |
| 8,224,070 | B2 | * | 7/2012 | Umemura et al. ........... 382/154 |
| 2004/0076323 | A1 | | 4/2004 | Fujii et al. |

FOREIGN PATENT DOCUMENTS

| | | |
|---|---|---|
| JP | 2001-326263 | 11/2001 |
| JP | 2004-93339 | 3/2004 |
| JP | 2006-300697 | 11/2006 |
| JP | 2007-199070 | 8/2007 |
| JP | 2008-058277 | 3/2008 |

* cited by examiner

METHOD OF MEASURING A THREE-DIMENSIONAL SHAPE

CROSS REFERENCE TO RELATED APPLICATION

This application is a divisional application of U.S. patent application Ser. No. 12/575,768, filed on Oct. 8, 2009 (currently pending), the disclosure of which is herein incorporated by reference in its entirety. The U.S. patent application Ser. No. 12/575,768 claims priority from and the benefit of Korean Patent Application No. 10-2008-0100003, filed on Oct. 13, 2008, which is hereby incorporated by reference for all purposes as if fully set forth herein.

BACKGROUND OF THE INVENTION

1. Field of the Invention

Exemplary embodiments of the present invention relate to a method of measuring a three-dimensional shape. More particularly, a method of measuring a three-dimensional shape capable of measuring a three-dimensional shape of a board by realigning an inspection area of the board using feature information extracted from CAD information of a bare board or feature information extracted from learning of the bare board.

2. Discussion of the Background

A conventional method of measuring a three-dimensional shape is explained in schematically as follows.

In order to measure a three-dimensional shape of a printed circuit board (PCB) (hereinafter, referred to as board, wherein the board includes solder formed thereon), the conventional method of measuring three-dimensional shape includes a two-dimensional inspection and a three-dimensional inspection.

In the two-dimensional inspection, two-dimensional lighting is illuminated onto a board, and a two-dimensional image reflected from the board is photographed and inspected by using a camera. In the three-dimensional inspection, a projector generates a pattern light and illuminates the pattern light onto a board, and a reflected pattern image is photographed and inspected by using a camera.

In the three-dimensional inspection, in case that phase information is obtained by using N-bucket algorithm, a grating of a projector is transferred at regular intervals by N-times to obtain N pattern images. After the N pattern images are obtained, phase information is obtained by using N-bucket algorithm, and height information of an inspection target in an inspection area of a board is produced by using the obtained phase information to thereby measure the three-dimensional shape.

When the phase information is obtained by using the N-bucket algorithm to measure the three-dimensional shape of the board, the board may be warped or contracted in a process of forming solder on the board or for other reasons.

When the board is warped or contracted, the defined inspection area is distorted. When the defined inspection area is distorted, the conventional method of measuring a three-dimensional shape may not detect the distortion of the inspection area, and thus the conventional method may not precisely measure a three-dimensional shape.

SUMMARY OF THE INVENTION

Exemplary embodiments of the present invention provide a method of measuring a three-dimensional shape capable of measuring a three-dimensional shape of a board by realigning an inspection area of the board, using feature information extracted from CAD information for a bare board or feature information extracted from learning a bare board.

Exemplary embodiments of the present invention also provide a method of measuring a three-dimensional shape capable of precisely measuring a three-dimensional shape of a board by realigning an inspection area of the board, using feature information extracted from CAD information for a bare board or feature information extracted from learning a bare board and inspecting the inspection area.

Additional features of the invention will be set forth in the description which follows, and in part will be apparent from the description, or may be learned by practice of the invention.

An exemplary embodiment of the present invention discloses a method of measuring a three-dimensional shape. The method includes reading feature information from a database, transferring a board to a measurement position, transferring a measurement head to an inspection area of the board, illuminating light of a first lighting device for three-dimensional measurement and light of a second lighting device for two-dimensional measurement onto the inspection area to photograph a first reflection image and a second reflection image that are reflected from the inspection area, realigning the inspection area by comparing the feature information with at least one of the photographed first and second reflection images to inspect distortion of the inspection area, and inspecting the realigned inspection area.

An exemplary embodiment of the present invention discloses a three-dimensional shape measuring apparatus. The three-dimensional shape measuring apparatus includes a stage transferring a target board to a measurement position, at least one projector illuminating pattern light onto an inspection area of the target board, a two-dimensional lighting section illuminating light for two-dimensional measurement onto the inspection area of the target board, a camera section photographing a pattern image and a two-dimensional image reflected from the target board, and a control section reading feature information of the inspection area from a database. The control section realigns the inspection area by comparing the feature information with at least one of the photographed pattern image and the photographed two-dimensional image to inspect distortion of the inspection area.

According to the present invention, an inspection area of a board is realigned by using feature information extracted from CAD information for a bare board or feature information extracted from learning a bare board, and is inspected, thereby precisely measuring a three-dimensional shape of the board although the board is warped or contracted.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
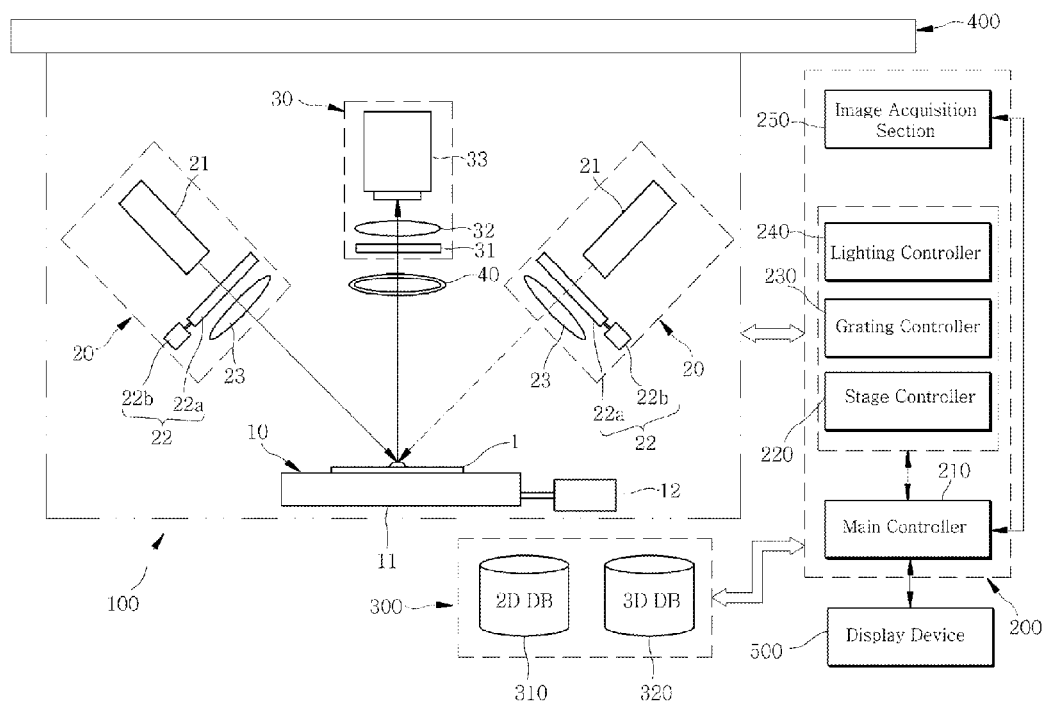
FIG. 1 is a schematic view illustrating a three-dimensional shape measuring apparatus to which a method of measuring a three-dimensional shape according to an exemplary embodiment of the present invention is applied.

The invention is described more fully hereinafter with reference to the accompanying drawings, in which embodiments of the invention are shown. This invention may, however, be embodied in many different forms and should not be construed as limited to the embodiments set forth herein. Rather, these exemplary embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

It will be understood that when an element or layer is referred to as being "on" or "connected to" another element or layer, it can be directly on or directly connected to the other element or layer, or intervening elements or layers may be present. In contrast, when an element is referred to as being "directly on" or "directly connected to" another element or layer, there are no intervening elements or layers present.

Hereinafter, a method of measuring a three-dimensional shape according to an exemplary embodiment of the present invention will be described with reference to the accompanying drawings.

Figure 2:
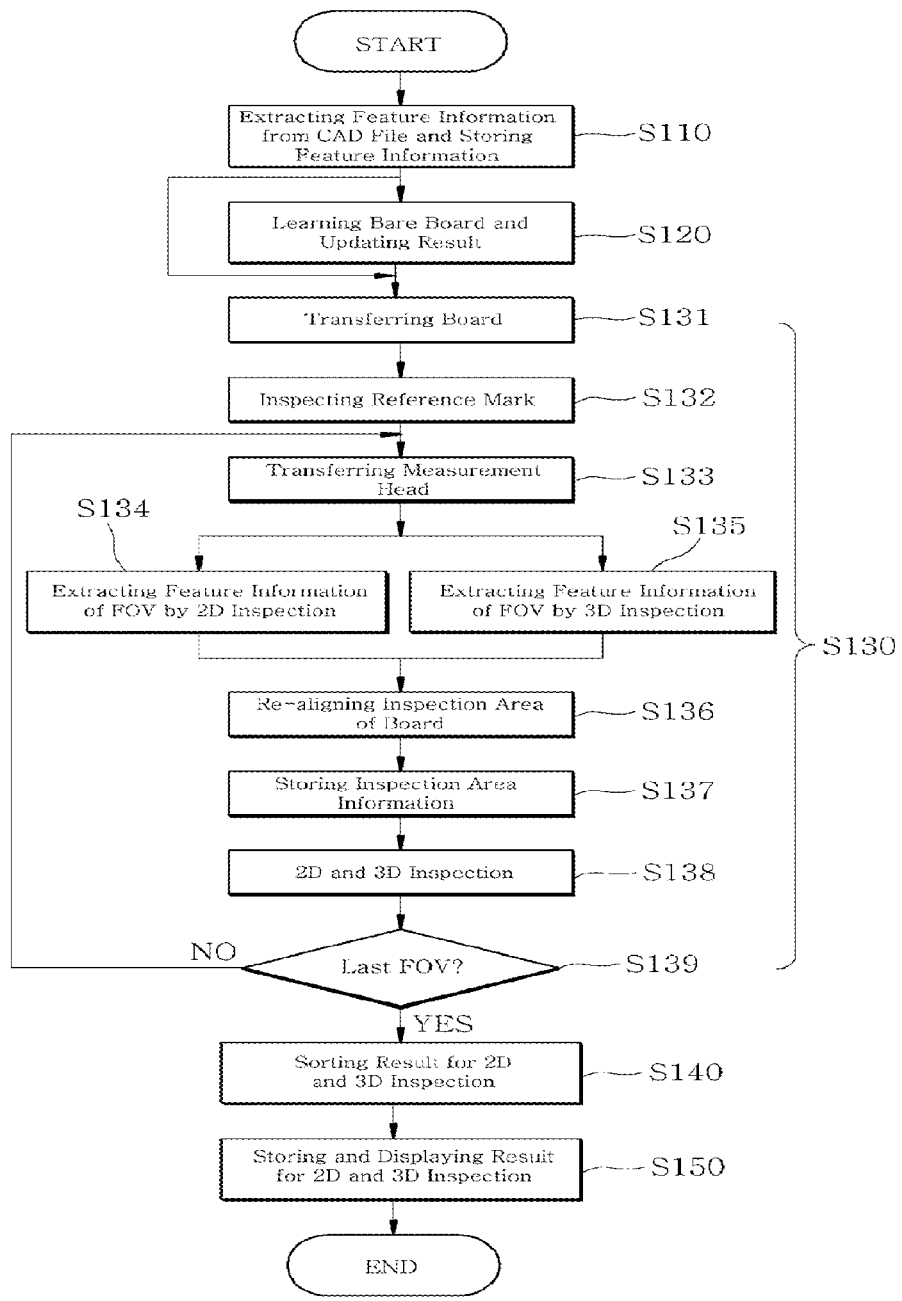
FIG. 2 is a flow chart illustrating a method of measuring three-dimensional shape in accordance with an exemplary embodiment of the present invention.
Figure 3:
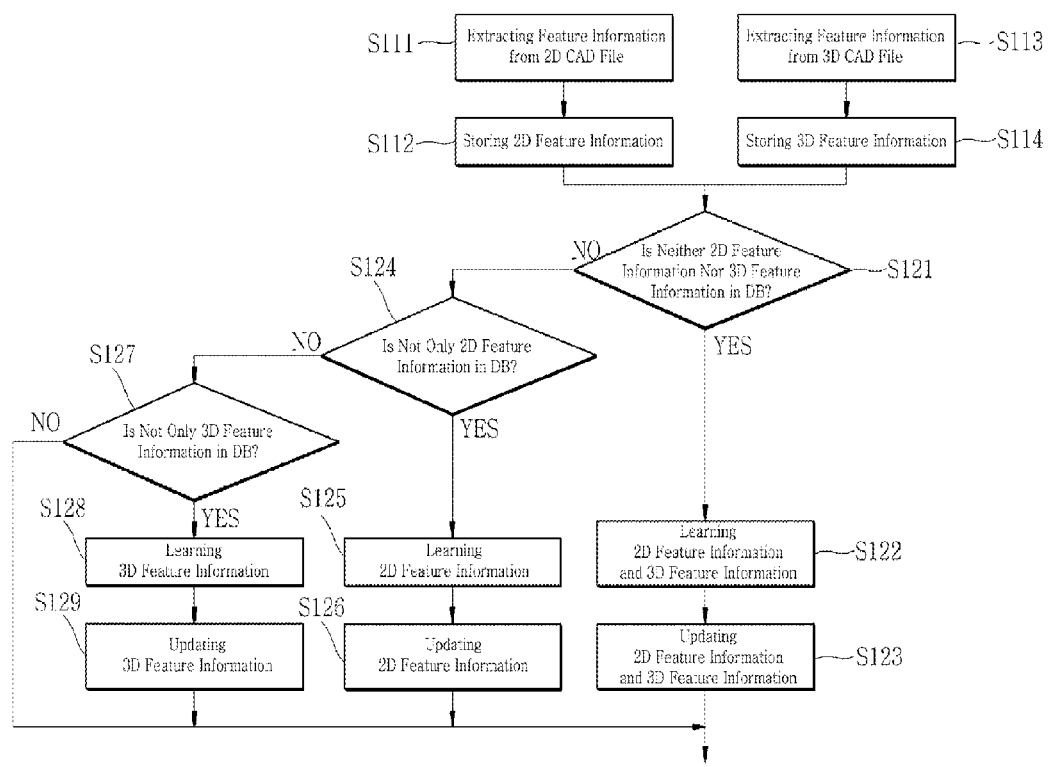
FIG. 3 is a flow chart illustrating a method of learning the bare board in FIG. 2.
Figure 4A:
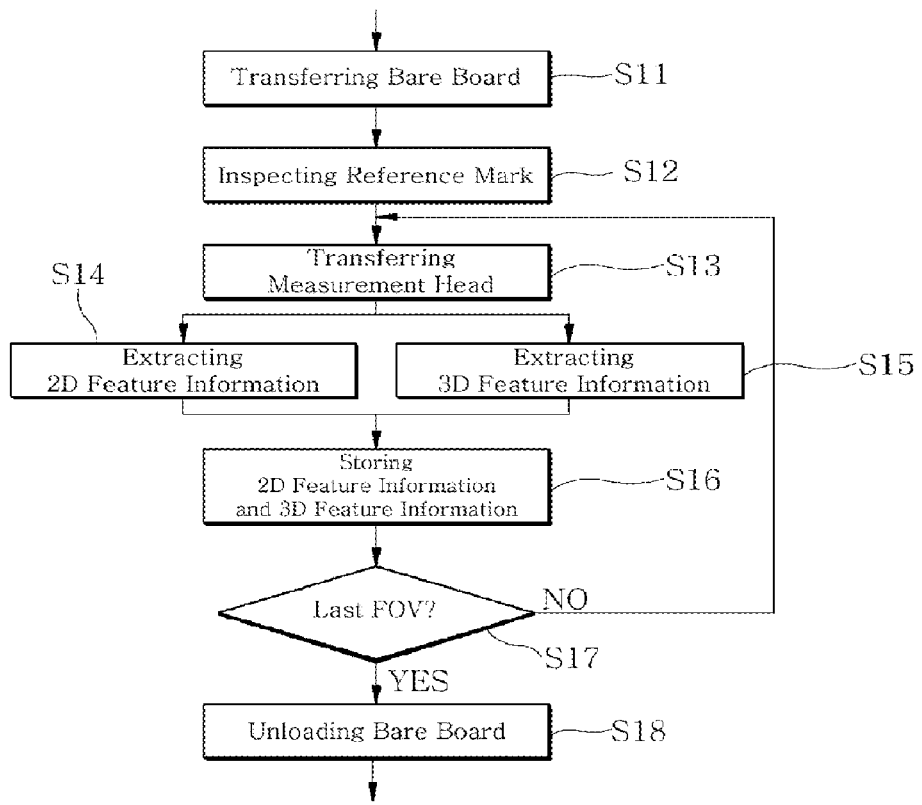
FIGS. 4A to 4C are flow charts illustrating a method of learning feature information in FIG. 3.
Figure 4B:
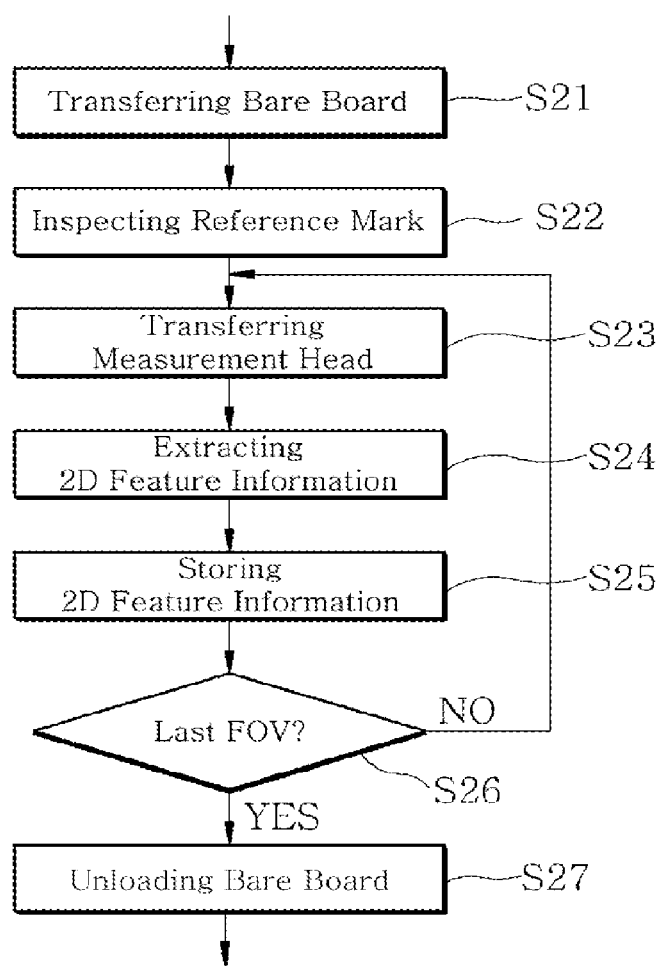
Figure 4C:
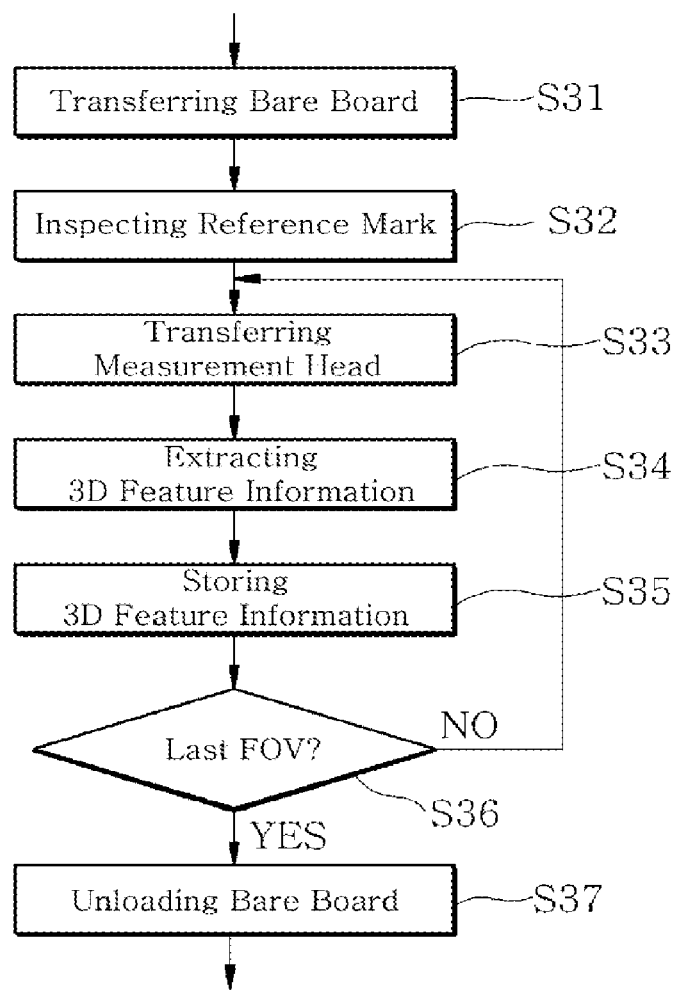

FIG. 1 is a schematic view illustrating a three-dimensional shape measuring apparatus to which a method of measuring a three-dimensional shape according to an exemplary embodiment of the present invention is applied. FIG. 2 is a flow chart illustrating a method of measuring three-dimensional shape in accordance with an exemplary embodiment of the present invention. FIG. 3 is a flow chart illustrating a method of learning the bare board in FIG. 2.

Before describing a method of measuring a three-dimensional shape according to an exemplary embodiment of the present invention, illustrated in FIGS. 1 to 3, a three-dimensional shape measuring apparatus to which the method of measuring a three-dimensional shape is applied will be schematically described.

Referring to FIG. 1, a three-dimensional shape measuring apparatus includes a measurement head 100, a control section 200, a database 300, a measurement head transfer section 400 and a display device 500.

The measurement head 100 may include a transfer stage 10, a plurality of projectors 20 and a camera section 30. The transfer stage 10 transfers an x/y stage 11 and a stage transfer device 12. The stage transfer device 12 transfers the x/y stage 11 in an x-axis direction and/or y-axis direction, to thereby transfer a bare board 1 (refer to FIGS. 6A and 7A) or a board 2 (refer to FIGS. 6B and 7B). The board 2 includes the bare board 1 and a solder 2a (refer to FIG. 6B) formed on the bare board 1.

Each of the projectors 20 may include a lighting device 21, a grating part 22 and a condensing lens 23. For example, the grating part 22 may include a grating 22a and a grating transfer device 22b. The grating 22a changes light from the lighting device 21 into pattern light to illuminate the pattern light onto the bare board 1 or the board 2. The grating transfer device 22b transfers the grating 22a at a regular interval. The condensing lens 23 is installed under the grating part 22 to receive and condense the pattern light, thereby providing the condensed pattern light to the bare board 1 or the board 2.

The camera section 30 may include a filter 31, an imaging lens 32 and a camera 33 to obtain a two-dimensional image or a pattern image. A two-dimensional lighting section 40 is installed under the camera section 30. The two-dimensional lighting section 40 generates two-dimensional light and illuminates the two-dimensional light onto the bare board 1 or the board 2 in two-dimensional inspection. The above-described measurement head 100 is transferred in an x-axis direction or a y-axis direction by the measurement head transfer section 400.

The control section 200 may include a main controller 210, a stage controller 220, a grating controller 230, a lighting controller 240 and an image acquisition section 250. The main controller 210 may wholly control the three-dimensional shape measuring apparatus. The stage controller 220 controls the transfer stage 10, and the grating controller 230 controls the grating transfer device 22b. The lighting controller 240 controls the lighting device 21 of the projector 20 and the two-dimensional lighting section 40. The image acquisition section 250 image-processes the pattern image or the two-dimensional image obtained by the camera section 30 to transfer the image-processed pattern image or the image-processed two-dimensional image to the main controller 210.

The database 300 stores CAD information having two-dimensional information and three-dimensional information of the bare board 1. The two-dimensional information of the CAD information is stored in a two-dimensional database 310, and three-dimensional information of the CAD information is stored in a three-dimensional database 320. The database 300 may be connected to the main controller 210, and, according to the request of the main controller 210, transfers the CAD information to the main controller. Alternatively, when two-dimensional feature information and three-dimensional feature information of the bare board 1 is produced in the main controller 210, the database 300 may receive the produced feature information and update the CAD information.

The display device 500 may display status of the three-dimensional shape measuring apparatus according to the control of the control section 200, and/or display the result of the two-dimensional and three-dimensional inspection generated in the main controller 210.

A method of measuring the three-dimensional shape of the board 2 by using the three-dimensional shape measuring apparatus will be described as follows.

Figure 5:
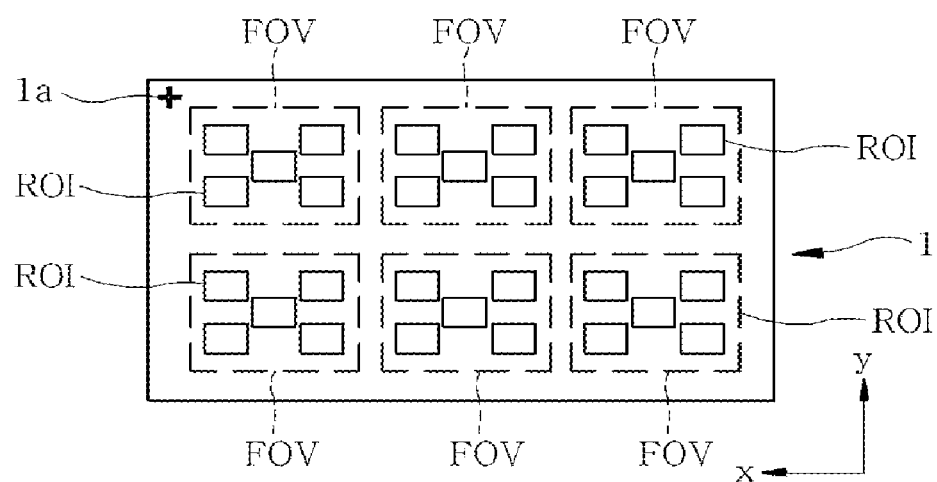
FIG. 5 is a plan view illustrating the bare board illustrated in FIG. 1.

As shown in FIGS. 1 to 3, firstly, when there exists a CAD file for the bare board 1 of the board 2, which is a measurement target, feature information of each inspection area (or field of view) FOV of the bare board 1 is extracted from the CAD file by using information of a defined inspection area FOV, and stored in the database 300 in step S110. The CAD file may be drawn up by designing the bare board 1 using a CAD program, and feature information of each inspection area FOV that is defined on the bare board 1 from the CAD file in advance is extracted from the control section 200. As shown in FIG. 5, a plurality of the inspection areas FOV are defined on one bare board 1, based on a reference mark 1a (refer to FIG. 5), and a plurality of interest areas (or regions of interest) ROI is defined in each inspection area FOV. The inspection area FOV and the interest area ROI may be defined by using the control section 200 in advance.

After the feature information of each inspection area of the bare board 1 extracted from the CAD file is stored, prior to inspecting the board 2, the control section 300 reads the feature information of each inspection area of the bare board 1, which is extracted from the CAD file, from the database 300. In case that there does not exist the CAD file for the bare board 1 in the database 300, each inspection area FOV of the bare board 1 is two-dimensionally and three-dimensionally inspected to learn the feature information of the bare board 1 by using the information of the defined inspection area FOV, and the result of learning the feature information is updated into the database 300 in step S120. That is, in case that there does not exist the feature information of the bare board 1 in the database 300, learning is performed the control section 200 so as to extract the feature information of the bare board 1.

After the feature information of the bare board 1 is extracted through the above-described processes, it is inspected whether each inspection area FOV of the board 2 is distorted or not due to warp or contraction of the board 2 by using the feature information extracted from CAD file and stored in the database 300 or the feature information extracted through learning and updated into the database 300, and each inspection area FOV of the board 2 is aligned, thereby storing inspection area information of the board 2 in step S130. After the inspection area information of the board 2 is stored, the board 2 is two-dimensionally inspected and three-dimensionally inspected by using the inspection area information of the board 2 to measure a three-dimensional shape of the board 2 in step S140.

Each step for the method of measuring a three-dimensional shape according to an exemplary embodiment of the present invention will be described in detail as follows.

In step S110 that the feature information of each inspection area FOV of the bare board 1 is extracted from the CAD file and stored in the database 300, in case that there exists a two-dimensional CAD file the bare board 1 for the board 2, two-dimensional feature information of each inspection area FOV of the bare board 1 is extracted from the two-dimensional CAD file by using the information of the defined inspection area FOV in step S111. After the two-dimensional feature information of each inspection area FOV of the bare board 1 is extracted from the two-dimensional CAD file, the two-dimensional feature information is stored in the database 300 in step S112.

After the two-dimensional feature information is stored in the database 300, in case that there exists a three-dimensional CAD file for the bare board 1 of the board 2, which is a measurement target, three-dimensional feature information of each inspection area FOV of the bare board 1 is extracted from the three-dimensional CAD file by using the information of the defined inspection area FOV in step S113. After the three-dimensional feature information of each inspection area FOV of the bare board 1 is extracted from the three-dimensional CAD file, the three-dimensional feature information is stored in the database 300 in step S114.

Figure 6A:
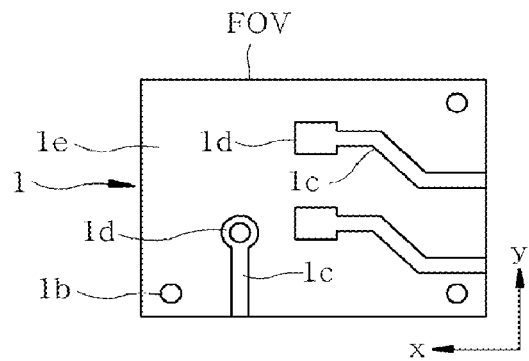
FIG. 6A to 6C are enlarged plan views illustrating the inspection area of the bare board or the board illustrated in FIG. 5.
Figure 7A:
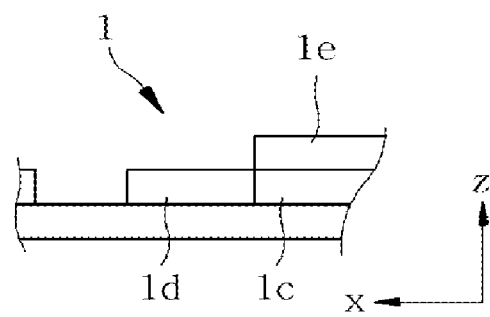
FIGS. 7A and 7B are enlarged cross-sectional views illustrating the interest area of the bare board or the board illustrated in FIG. 5.

The two-dimensional feature information of each inspection area FOV of the bare board 1 from the two-dimensional CAD file and the three-dimensional feature information of each inspection area FOV of the bare board 1 from three-dimensional CAD file may include, as shown in FIG. 6A, information of position coordinates, a size, an image and a border line for a reference mark 1*a*, a hole 1*b*, a lead pattern 1*c*, a pad 1*d* and a silk pattern 1*e*, which are located in each inspection area FOV of the bare board 1 in the CAD file, and the image information may be stored corresponding to the inspection area FOV and the interest area ROI. The feature information extracted from learning may be substantially the same as the three-dimensional feature information of each inspection area FOV of the bare board 1 obtained by using the CAD file.

In step S120 that the feature information of the bare board 1 is learned and the result of learning is updated into the database 300, it is inspected whether the two-dimensional feature information and the three-dimensional feature information of the bare board 1 is in the database 300 or not in step S121. When neither the two-dimensional feature information nor the three-dimensional feature information is in the database 300, each inspection area FOV of the bare board 1 is two-dimensionally and three-dimensionally inspected by using the information of the defined inspection area FOV to learn the two-dimensional feature information and the three-dimensional feature information of the bare board 1 in step S122. After the two-dimensional feature information and the three-dimensional feature information of the bare board 1 is learned, the learned two-dimensional feature information and the learned three-dimensional feature information of the bare board 1 is updated into the database 300 in step S123.

In step S121 that it is inspected whether the two-dimensional feature information and the three-dimensional feature information of the bare board 1 is in the database 300 or not, in case that at least one of the two-dimensional feature information and the three-dimensional feature information of the bare board 1 is in the database 300, it is inspected that only the two-dimensional feature information of the bare board 1 is not in the database 300 in step S124. When only the two-dimensional feature information is not in the database 300, each inspection area FOV of the bare board 1 is two-dimensionally inspected by using the information of the defined inspection area FOV to learn the two-dimensional feature information of the bare board 1 in step S125. After the two-dimensional feature information of the bare board 1 is learned, the learned two-dimensional feature information of the bare board 1 is updated into the database 300 in step S126.

In step S124 that it is inspected whether only the two-dimensional feature information of the bare board 1 is not in the database 300, in case that it is not that only the two-dimensional feature information of the bare board 1 is not in the database 300, it is inspected that only the three-dimensional feature information of the bare board 1 is not in the database 300 in step S127. When only the three-dimensional feature information is not in the database 300, each inspection area FOV of the bare board 1 is three-dimensionally inspected by using the information of the defined inspection area FOV to learn the three-dimensional feature information of the bare board 1 in step S128. After the three-dimensional feature information of the bare board 1 is learned, the learned three-dimensional feature information of the bare board 1 is updated into the database 300 in step S129.

Hereinafter, steps S122, S125 and S128 of the above-described steps S121 to S129 will be described in detail with reference to the accompanying drawings of FIGS. 1 and 4A to 4C.

In step S122 that each inspection area FOV of the bare board 1 is two-dimensionally and three-dimensionally inspected to learn the two-dimensional feature information and the three-dimensional feature information of the bare board 1, firstly, in case that neither the two-dimensional feature information nor the three-dimensional feature information of the bare board 1 is in the database 300, the bare board 1 is transferred to a measurement position by the stage transfer device 10 in step S11. After the bare board 1 is transferred, the reference mark 1a (refer to FIG. 5) of the bare board 1 is inspected by using the measurement head 100 in step S12. After the reference mark 1a of the bare board 1 is inspected, the measurement head 100 is transferred to the inspection area FOV based on the reference mark 1a in step S13. The measurement head 100 is transferred by the measurement head transfer device 400.

After the measurement head 100 is transferred to the inspection area FOV of the bare board 1, the projector 20 and the two-dimensional lighting section 40 are alternately operated to generate and illuminate pattern light and two-dimensional light onto the inspection area FOV, and thus reflected pattern image and two-dimensional image is photographed by the camera section 30 to extract the two-dimensional feature information and the three-dimensional feature information of the inspection area FOV in steps S14 and S15. After the two-dimensional feature information and the three-dimensional feature information is extracted, the two-dimensional feature information and the three-dimensional feature information is stored in step S16. After the two-dimensional feature information and the three-dimensional feature information is stored, it is inspected whether the inspection area FOV in which the two-dimensional feature information and the three-dimensional feature information is extracted and stored is the last inspection area FOV or not in step S17. In case that the inspection area FOV in which the two-dimensional feature information and the three-dimensional feature information is extracted and stored is the last inspection area FOV, the bare board 1 is unloaded in step S18. In case that the inspection area FOV in which the two-dimensional feature information and the is three-dimensional feature information is extracted and stored is not the last inspection area FOV, the present process returns to step S13 that the measurement head 100 is transferred to the inspection area FOV based on the reference mark 1a.

In step S125 that each inspection area FOV of the bare board 1 is two-dimensionally inspected to learn the two-dimensional feature information of the bare board 1, firstly, in case that only the two-dimensional feature information of the bare board 1 is not in the database 300, the bare board 1 is transferred to a measurement position by the stage transfer device 10 in step S21. After the bare board 1 is transferred, the reference mark 1a of the bare board 1 is inspected by using the measurement head 100 in step S22. After the reference mark 1a of the bare board 1 is inspected, the measurement head 100 is transferred to the inspection area FOV based on the reference mark 1a in step S23. After the measurement head 100 is transferred to the inspection area FOV of the bare board 1, the two-dimensional lighting section 40 is operated to generate and illuminate the two-dimensional light onto the inspection area FOV, and thus reflected two-dimensional image is photographed by the camera section 30 to extract the two-dimensional feature information of the inspection area FOV in step S24.

After the two-dimensional feature information is extracted, the two-dimensional feature information is stored in step S25. After the two-dimensional feature information is stored, it is inspected whether the inspection area FOV in which the two-dimensional feature information is extracted and stored is the last inspection area FOV or not in step S26. In case that the inspection area FOV in which the two-dimensional feature information is extracted and stored is the last inspection area FOV, the bare board 1 is unloaded in step S27. In case that the inspection area FOV in which the two-dimensional feature information is extracted and stored is not the last inspection area FOV, the present process returns to step S23 that the measurement head 100 is transferred to the inspection area FOV based on the reference mark 1a.

In step S128 that each inspection area FOV of the bare board 1 is three-dimensionally inspected to learn the three-dimensional feature information of the bare board 1, in case that only the three-dimensional feature information of the bare board 1 is not in the database 300, the bare board 1 is transferred to a measurement position by the stage transfer device 10 in step S31. After the bare board 1 is transferred, the reference mark 1a of the bare board 1 is inspected by using the measurement head 100 in step S32. After the reference mark 1a of the bare board 1 is inspected, the measurement head 100 is transferred to the inspection area FOV based on the reference mark 1a in step S33.

After the measurement head 100 is transferred to the inspection area FOV of the bare board 1, the projector 20 is operated to generate and illuminate the pattern light onto the inspection area FOV, and thus the reflected pattern image is photographed by the camera section 30 to extract the three-dimensional feature information of the inspection area FOV in step S34. After the three-dimensional feature information is extracted, the three-dimensional feature information is stored in step S35. After the three-dimensional feature information is stored, it is inspected whether the inspection area FOV in which the three-dimensional feature information is extracted and stored is the last inspection area FOV or not in step S35. In case that the inspection area FOV in which the three-dimensional feature information is extracted and stored is the last inspection area FOV, the bare board 1 is unloaded in step S36. In case that the inspection area FOV in which the three-dimensional feature information is extracted and stored is not the last inspection area FOV, the present process returns to step S33 that the measurement head 100 is transferred to the inspection area FOV based on the reference mark 1a.

In step S130 that after it is inspected whether each inspection area FOV of the board 2 is distorted or not, each inspection area FOV of the board 2 is aligned, thereby storing the inspection area information of the board 2, and the board 2 is two-dimensionally inspected by using the inspection area information of the board 2, as shown in FIGS. 1 and 2, firstly, the board 2 (refer to FIG. 6A) is transferred to a measurement position by the stage transfer device 10 in step S131. After the board 2 is transferred, the reference mark 1a of the board 2 is inspected by using the measurement head 100 in step S132. After the reference mark 1a of the board 2 is inspected, the measurement head 100 is transferred to the inspection area FOV based on the reference mark 1a in step S133. The inspection area FOV of the board 2 may be defined by substantially the same method as the inspection area FOV of the bare board 1 illustrated in FIG. 5.

Figure 6B:
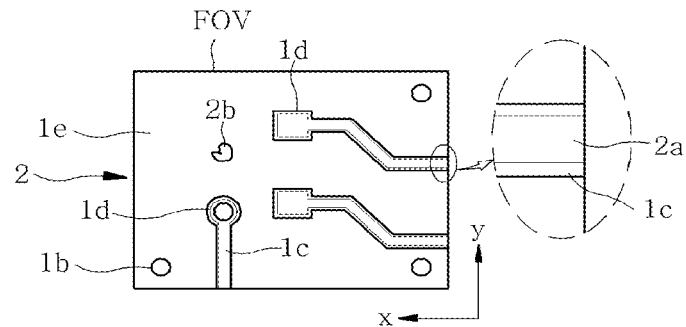
Figure 7B:
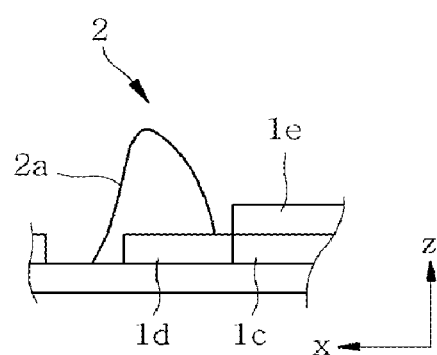

After the measurement head 100 is transferred to the inspection area FOV, the projector 20 and the two-dimensional lighting section 40 are alternately operated to generate and illuminate pattern light and two-dimensional light onto the inspection area FOV of the board 2, and thus reflected pattern image and two-dimensional image is photographed by the camera section 30, which corresponds to two-dimensional inspection and three-dimensional inspection, to extract the two-dimensional feature information and the three-dimensional feature information of the inspection area FOV in steps S134 and S135. The two-dimensional feature information and the three-dimensional feature information of each inspection area FOV of the board 2 may include, as shown in FIGS. 6B and 7B, information of position coordinates, a size, an image and a border line for a reference mark 1a, a hole 1b, a lead pattern 1c, a pad 1d and a silk pattern 1e, which are located in each inspection area FOV of the board 2, and the image information may be stored corresponding to the inspection area FOV and the interest area ROI.

After the two-dimensional the feature information and the three-dimensional feature information of the inspection area FOV is extracted, it is inspected whether each defined inspection area FOV is distorted or not due to warp or contraction of the board 2 by using the feature information extracted from CAD file and stored in the database 300 or the feature information extracted through learning and updated into the database 300, and the inspection area FOV of the board 2 is realigned in step S136. That is, in step S136, the two-dimensional feature information and the three-dimensional feature information of the inspection area FOV, which is extracted by the two-dimensional inspection and the three-dimensional inspection, is compared with the feature information extracted from the CAD file and stored in the database 300 or the feature information extracted through learning and updated into the database 300, and thus, in case that there exists difference, it is determined that the board 2 is distorted due to warp or contraction of the board 2, thereby realigning the inspection area FOV.

Figure 6C:
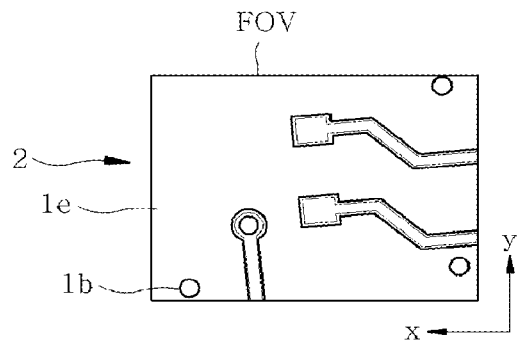

The realignment of the inspection area FOV is performed by the control section 200. The control section 200 in case that the reference mark 1a, the hole 1b, the lead pattern 1c, the pad 1d, the silk pattern 1e, etc., which are located in the inspection area FOV of the board 2, as shown in FIGS. 6B and 7B, are transformed in the x-axis direction or the y-axis direction, as shown in FIG. 6C, when feature information that is produced by coordinate relation of x-axis and y-axis, i.e., coordinate difference serving as transformation amount of the inspection area FOV of the board 2 is extracted by using the feature information of the bare board 1 in FIG. 6A or the feature information extracted from the CAD file, the inspection area FOV of the board 2 is corrected and realigned by using the feature information. When the inspection area FOV of the board 2 is realigned by using the feature information of the bare board 1, the bare board 1 having no or little distortion is used.

After the inspection area FOV of the board 2 is realigned, the inspection area information of the board 2 is stored in step S137. That is, after the inspection area FOV of the board 2 is realigned by using the feature information of the inspection area FOV of the board 2, the inspection area information is stored.

After the inspection area information of the board 2 is stored, the projector 20 of the measurement head 100 and the two-dimensional lighting section 40 are alternately operated to generate and illuminate pattern light and two-dimensional light onto the inspection area FOV of the board 2 according to the inspection area information, and thus reflected pattern image and two-dimensional image is photographed by the camera section 30, thereby two-dimensionally and three-dimensionally inspecting the inspection area FOV of the board 2 in step S138. That is, when the inspection area FOV of the board 2 is distorted, the distortion is corrected to realign the inspection area FOV, and thus the inspection area FOV of the board 2 is, alternately, two-dimensionally and three-dimensionally inspected.

In case that the inspection area FOV of the board 2 is, alternately, two-dimensionally and three-dimensionally inspected, since a lead pattern 1c, a pad 1d and a silk pattern 1e are easily distinguishable shown in FIGS. 5, 6A to 6C, 7A and 7b by the two-dimensional inspection, three-dimensional inspection may be more precisely performed. In addition, since shapes of the lead pattern 1c, the pad 1d and a solder 2a may be easily extracted by the three-dimensional inspection, a foreign substance 2b that is not easily distinguishable in two-dimensional inspection may be easily extracted.

After the two-dimensional inspection and three-dimensional inspection, it is inspected whether the inspection area FOV of the board 2 is the last or not in step S139. Thereafter, in case that the inspection area FOV of the board 2 is not the last, the present process returns to step S133 that the measurement head 100 is transferred to the inspection area FOV. That is, after the inspection result for the inspection area FOV of the board 2 is stored as the inspection area information, the inspection area FOV of the board 2 is corrected, and the corrected inspection area FOV is two-dimensionally and three-dimensionally inspected so as to measure the three-dimensional shape of the board 2, thereby successively inspecting all of the inspection area FOV of the board 2.

After the two-dimensional inspection and the three-dimensional inspection is performed by using the inspection area information of the board 2, the result for the two-dimensional inspection and the three-dimensional inspection is sorted, stored and displayed in step S140 and S150. That is, after the two-dimensional inspection and the three-dimensional inspection is performed, the control section 200 stores the result, and displays the result in the display device 500 so as to easily review the result, thereby completing the two-dimensional inspection for the board 2 or the measurement of the three-dimensional shape.

The method of measuring a three-dimensional shape according to the present invention may be employed in measuring a three-dimensional shape of a printed circuit board, electronic element, etc.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A three-dimensional shape measuring apparatus comprising:
a stage transferring a target board to a measurement position;
at least one projector illuminating pattern light onto an inspection area of the target board;
a two-dimensional lighting section illuminating light for two-dimensional measurement onto the inspection area of the target board;
a camera section photographing a pattern image and a two-dimensional image reflected from the target board; and
a control section reading feature information of the inspection area from a database,
wherein the control section realigns the inspection area by comparing the feature information with at least one of the photographed pattern image and the photographed two-dimensional image to inspect distortion of the inspection area.

2. The three-dimensional shape measuring apparatus of claim 1, wherein the feature information includes at least one of each information for a reference mark, a hole, a lead pattern, a pad and a silk pattern of a bare board of the target board.

3. The three-dimensional shape measuring apparatus of claim 1, in case that the feature information is not in the database, the feature information of the bare board is learned and stored by using information of the realigned inspection area.

4. The three-dimensional shape measuring apparatus of claim 1, wherein the projector includes a light source, a grating, a grating transfer device transferring the grating by N-times and a condensing lens.

5. The three-dimensional shape measuring apparatus of claim 4, wherein at least one projector comprises a plurality of projectors, and the projectors illuminate pattern light onto the inspection area in different directions from each other.

6. The three-dimensional shape measuring apparatus of claim 5, wherein the projectors employ multi wavelengths.

7. The three-dimensional shape measuring apparatus of claim 1, wherein the control section divides the inspection area into a plurality of interest areas, wherein the inspection area is realigned for each interest area.

* * * * *